United States Patent [19]

Peets et al.

[11] Patent Number: 5,002,764
[45] Date of Patent: Mar. 26, 1991

[54] TREATMENT OF ACTINIC KERATOSES WITH ALPHA$_2$ INTERFERON

[75] Inventors: Edwin A. Peets, New York, N.Y.; Kenneth A. Smiles, East Windsor, N.J.; Daniel J. Tanner, Brooklyn, N.Y.

[73] Assignee: Schering Corporation, Kenilworth, N.J.

[21] Appl. No.: 397,365

[22] Filed: Aug. 22, 1989

Related U.S. Application Data

[63] Continuation of Ser. No. 896,169, Aug. 12, 1986, abandoned.

[51] Int. Cl.$^5$ ............................................... A61K 37/66
[52] U.S. Cl. ................................ 424/85.7; 424/85.4
[58] Field of Search .................... 424/85.4, 85.5, 85.6, 424/85.7

[56] References Cited

U.S. PATENT DOCUMENTS 4,605,555 8/1986 Sato et al. .............................. 424/85

FOREIGN PATENT DOCUMENTS 77063 4/1983 European Pat. Off. .
83101198 4/1983 World Int. Prop. O. .

OTHER PUBLICATIONS

Yancey et al., *Am. Acad. Dermatol.,* 3, No. 6 (1980), 585–595.
Rubenstein, *Biochem. Biophys. Acta,* 695 (1982), 5–16.
Nagata et al., *Nature,* 284, (1980), 316–320.
Edwards et al., *Arch. Dermatol.,* 122 (Jul., 1986) pp. 779–782.
Langer et al. J. of Invest. Dermatology 83, (1984), pp. 1285–1365.
Yusk, Current Therapy, ed. Comm, pp. 643–645, 1979.
Ikic et al., The Lancet, pp. 1025–1027, May 9, 1981.

*Primary Examiner*—Howard E. Schain
*Assistant Examiner*—Choon Koh
*Attorney, Agent, or Firm*—Anita W. Magatti; Thomas D. Hoffman

[57] ABSTRACT

A method of treating actinic keratoses with alpha$_2$ interferon is disclosed.

6 Claims, No Drawings

TREATMENT OF ACTINIC KERATOSES WITH ALPHA$_2$ INTERFERON

This is a continuation of application Ser. No. 06/896,169 filed Aug. 12, 1986.

Summary of the Invention

This invention relates to a method of treating actinic keratoses with recombinant human alpha interferon by administering the interferon directly into the lesion, i.e., intralesionally.

In particular, this invention relates to a specific dosage regimen for administering alpha$_2$ interferon in the treatment of actinic keratoses.

Background

Actinic keratoses represent areas of dysplastic keratinocytes which develop within the epidermis in response to chronic exposure to ultraviolet radiation. These erythematous, scaling lesions are a cosmetic nuisance and may cause tenderness or pruritus in some patients. More importantly, some actinic keratoses progress into invasive squamous cell carcinomas which are not only locally destructive, but also may rarely metastasize. Although there are several efficient methods of removing actinic keratoses, including liquid nitrogen cryotherapy, topical 5-fluorouracil and surgical excision, each of these is destructive. A treatment which could nontraumatically remove actinic keratoses would be of great benefit to patients.

Interferons are a family of proteins which exhibit antiviral activity against certain viruses and anticancer activity against certain cancers. There are three types of interferons: alpha or leukocyte interferon, beta or fibroblast interferon and gamma or immune interferon. Human alpha interferon is a naturally occurring mixture of at least eleven components including those designated alpha-1 interferon and alpha-2 interferon. Human alpha interferon exhibiting biological properties similar to those of naturally occurring human leukocyte interferon can be made by recombinant methods.

The anticancer activity of alpha interferon is based on its anti-proliferative action. It has been suggested that because interferons possess antiproliferative activity, alpha interferon might be useful in the treatment of proliferative diseases of the skin such as psoriasis (See K. B. Yancey and J. G. Smith, Jr., "Interferon: Status in treatment of skin disease", *Am. Acad. Dermatol.*, 3, No. 6 (1980), 585–595), but no report of the treatment of actinic keratoses has been published.

A number of alpha interferon species or components are known and are usually designated by a numeral after the Greek letter alpha, and all are contemplated for use in this invention. Thus, the species designated human alpha-1 interferon and human alpha-2 interferon (sometimes called human alpha-2b interferon or abbreviated hIFN-α2; USAN: Interferon Alfa-2b) are contemplated, with human alpha-2 interferon preferred. Alpha-2 interferon can be produced in bacteria using recombinant techniques as disclosed in Rubenstein, *Biochem. Biophys. Acta*, 695, 5–16 (1982). In addition, alpha-2 interferon may be prepared by recombinant-DNA methods disclosed by Nagata et al., *Nature*, 284, 316–320 (1980), European Patent 32,134 and U.S. Pat. No. 4,289,690. Various alpha-2-interferon species are disclosed in U.S. Pat. No. 4,503,035.

Detailed Description

We have found that actinic keratoses favorably respond to intralesional injections of alpha2 interferon, and that this response is dose and dose schedule dependent. One study indicates that the concentration of alpha$_2$ interferon per dose is a significant factor in the treatment of actinic keratoses, and a second study indicates that some minimum dosage is required over a specified period of time. Following are detailed descriptions of those studies (i.e., Phase I and Phase II).

Patients and Methods

In Phase I of the study, the dose-dependency of the therapeutic effect was investigated.

Patients

Sixteen patients each having multiple lesions were divided into two groups, eight with predominantly hand and arm lesions, and eight with actinic keratoses of the face. Within each group, patients were randomly assigned to one of four treatment groups of two subjects each. Three typical actinic keratoses which were at least three centimeters apart from one another were selected on each subject. These lesions were then measured, characterized as to degree of erythema and scale, and photographed as a baseline evaluation before treatment. Scaling and erythema were quantitiated on a seven-point scale ranging from absent to marked. An additional one to four actinic keratoses were similarly evaluated, although not treated, in order to study the possible systemic effects of intralesional alpha interferon. The patients had received no therapy for their lesions during the six weeks prior to the study, and none had reported a history of exposure to radiation, tars, arsenic, or immunosuppressive agents. Acetaminophen, thiazide diuretics and potassium supplements were the only concommitant medications permitted during the study.

Laboratory Tests

Laboratory monitoring consisted of a pretreatment complete blood count with differential and a platelet count, blood chemistry analysis, and urinalysis. These were repeated weekly during therapy, and one week and one month after termination of therapy. An additional white blood cell count was done 24 hours after the first injection of the test medication. Serum interferon-neutralizing factor was assayed before treatment and at one and four weeks after completion of therapy.

Treatment

Treatments were conducted with reconstituted solutions of lyophilized human recombinant alpha2 interferon prepared immediately before injection by the addition of sterile water and normal saline to the lyophilizate to obtain the desired doses of $5 \times 10^5$ IU/0.1cc, $1 \times 10^5$ IU/0.1cc, and $1 \times 10^4$ IU/0.1cc. Treatment consisted of injections of one of the above doses of interferon or placebo into each of three designated actinic keratoses three times weekly for three weeks, for a total of nine injections. Placebo treated patients received the same course of treatment with 0.1cc injections of sterile water and normal saline. Patients were observed in the office for thirty minutes after the injections for symptoms and signs of systemic reactions to the treatment.

Response Criteria

The size of the treated and untreated lesions was measured and compared to the baseline measurement, and the degree of erythema and scaling was re-evaluated on the seven-point scale discussed above. Follow-up evaluations also included a global assessment of changes in lesion characteristics which was expressed in a sixpoint scale ranging from clear to exacerbation.

In Phase II of the study, five different dosing schedules were evaluated.

Patients

Forty five patients meeting the same criteria as in Phase I (except that any concommitant medication not known to interfere with interferon was permitted) were included. These patients were divided into five treatment groups.

Laboratory Tests

Same as Phase I.

Treatment

Treatments were conducted with reconstituted solutions of lyophilized human recombinant alpha$_2$ interferon. The alpha$_2$ interferon solutions were prepared immediately before injection by the addition of sterile water and normal saline to yield a dose of $5 \times 10^5$ IU per 0.1cc.

Within each of the five treatment groups, three patients received placebo, and from five to seven subjects received alpha$_2$ interferon, $5 \times 10^5$ IU per injection. Each treatment group was injected according to a different dosing regimen These regimens were 1) one injection per lesion, 2) three injections per lesion in one week, 3) three injections per lesion one week apart, 4) six injections per lesion over two weeks, and 5) nine injections per lesion over three weeks Where multiple injections were given, they were administered every other day (e.g., Monday, Wednesday and Friday).

Response Criteria

Evaluations of the actinic keratoses and adverse reactions, as described for Phase I, were carried out weekly during the treatment phase, and weekly or bimonthly in the post treatment phase.

The following Table 1 shows the results of the dose-dependence study (Phase I).

TABLE 1

Effect of 9 Injections of Alpha$_2$ Interferon at Variable Doses on Actinic Keratoses

| Treatment Group | Cleared | marked (75%*) Improvement | moderate (50%*) Improvement | mild (25%*) Improvement | No Change |
|---|---|---|---|---|---|
| $5 \times 10^5$ IU/Inj | 11 (92%) | 1 (8%) | | | |
| $1 \times 10^5$ IU/Inj | 5 (42%) | 6 (50%) | 1 (8%) | | |
| $1 \times 10^4$ IU/Inj | 7 (58%) | 1 (8%) | 2 (17%) | | 2 (17%) |
| Placebo | | 2 (17%) | 4 (33%) | 2 (17%) | 4 (33%) |

*percent improvement is measured by reduction in size and scaling

As is apparent from the data in Table 1, the therapeutic response of actinic keratoses to treatment with alpha$_2$ interferon is dose-dependent, that is, administration of higher doses has a greater therapeutic effect. Statistically, the difference in the improvement of the actinic keratoses treated with high dose alpha$_2$ interferon compared to treatment with placebo was significant at $P=0.01$.

The following Table 2 shows the results of the dosing schedule study.

TABLE 2

Effect of Different Dosing Schedules of Intralesional Alpha$_2$ Interferon ($5 \times 10^5$ IU) on Actinic Keratoses

| Treatment | Total # Lesions | Cleared | Marked (75%*) Improvement | Moderate (50%*) Improvement | Mild (25%*) Improvement | No Change |
|---|---|---|---|---|---|---|
| 1 Inj IFN | 18 | 2 (11%) | 5 (28%) | 4 (22%) | 3 (17%) | 4 (22%) |
| Placebo | 9 | | 1 (11%) | 7 (78%) | 1 (11%) | |
| 3 Inj/1 Wk IFN | 21 | 10 (48%) | 6 (29%) | 2 (10%) | 1 (5%) | 2 (10%) |
| Placebo | 9 | | 2 (20%) | 3 (33%) | 1 (11%) | 3 (33%) |
| 3 Inj/3 Wks IFN | 18 | 9 (50%) | 3 (17%) | 2 (11%) | 4 (22%) | |
| Placebo | 9 | 1 (11%) | 1 (11%) | | | 7 (78%) |
| 6 Inj/2 Wks IFN | 15 | 14 (93%) | 1 (7%) | | | |
| Placebo | 9 | 5 (56%) | 1 (11%) | 2 (22%) | 1 (11%) | |
| 9 Inj/3 Wks IFN | 15 | 7 (47%) | 3 (20%) | 3 (20%) | 2 (13%) | |
| Placebo | 9 | | 4 (44%) | 2 (22%) | | 3 (33%) |

*percent improvement is measured by reduction in size and scaling

Table 2 indicates that for a given dosage unit, i.e., $5 \times 10^5$ IU per injection, different numbers of injections (i.e., 1, 3, 6 or 9) over different lengths of time (i.e., once, 3/week, 3/3 weeks, 6/2 weeks and 9/3 weeks) produce different rates of response Reference to Table 2 indicates that one injection is no more effective than placebo, and that three injections, either in one week or over three weeks, produce poor response rates. Six injections over two weeks produce the greatest response (93% cleared), while in contrast to the results in Table 1, only 47% of the lesions treated with nine injections over three weeks cleared. While the discrepancy in the latter result is unexplained at present, it is clear from the data that at least $3 \times 10^6$ IU alpha interferon (i.e., the equivalent of six injections at $5 \times 10^5$ IU each) administered to each actinic keratosis lesion is necessary to produce a clinically important effect.

Interferon is able to exert its effects both locally and systemically. Although some patients did develop systemic side effects sometimes associated with intralesional injection of interferon (e.g., local inflammation, myalgias), the beneficial effects of intralesional interferon were most likely due to the local effect of a higher concentration of medication, since distant actinic keratoses were not significantly affected.

For intralesional administration, injectable pharmaceutically acceptable compositions are used. Such compositions can, for example, be prepared by diluting freeze dried hIFN-α2 with sterile preservative-free water to produce an isotonic solution containing the appropriate concentration of interferon Other injectable compositions using saline, aqueous dextrose, glycerol, ethanol and the like, to thereby form a solution or suspension for injection can also be used If desired, minor amounts of nontoxic auxiliary substances such as wetting or emulsifying agents, preservatives, pH buffering agents and the like, for example, sodium acetate or sorbitan monolaurate, can be incorporated into the compositions. Actual methods of preparing such dosage forms are known or will be apparent to those skilled in this art; see for example, *Remington's Pharmaceutical Sciences*, Mack Publishing Company, Easton, PA, 16th Edition, 1980.

In view of the inconvenience attendant to treatment with multiple injections (e.g the inconvenience of repeated office visits, the discomfort of the injection procedure), the use of a sustainedrelease formulation comprising alpha$_2$ interferon which releases the required amount of alpha$_2$ interferon over the required time period is contemplated. It is further contemplated that the treatment period may be reduced when a sustained release formulation is used since alpha$_2$ interferon is being constantly administered to the lesion, as opposed to the intermittant administration of alpha$_2$ interferon in the multiple-injection method.

We claim:

1. A method for treating actinic keratoses in humans comprising intralesionally administering to a human in need of such treatment a pharmaceutical composition comprising a sufficient amount of recombinant human alpha$_2$ interferon to be effective as an anti-actinic keratoses agent.

2. A method of claim 1 wherein the effective amount of alpha$_2$ interferon is at least $3 \times 10^6$ International Units.

3. A method of claim 1 wherein alpha$_2$ interferon is administered in divided dosages.

4. A method of claim 2 wherein the divided dosages are administered over a period of two to three weeks.

5. A method of claim 3 comprising the administration of $5 \times 10^5$ International Units of alpha$_2$ interferon three times a week for two to three weeks.

6. A method of claim 1 wherein the pharmaceutical composition comprising alpha$_2$ interferon is a sustained release composition.

* * * * *